United States Patent [19]

DiBerardino et al.

[11] Patent Number: 5,321,165

[45] Date of Patent: Jun. 14, 1994

[54] SYNTHETIC METHOD FOR ETHYNYLATION OF AROMATIC COMPOUNDS

[75] Inventors: Thomas DiBerardino, Severna Park, Md.; Patricia M. Lutz, Lincroft, N.J.; Barbara F. Howell, Arnold, Md.

[73] Assignee: The United States of America as represented by the Secretary of the Navy, Washington, D.C.

[21] Appl. No.: 75,933

[22] Filed: Jun. 14, 1993

[51] Int. Cl.$^5$ ...................... C07C 45/61; C07C 45/00
[52] U.S. Cl. .................................. 568/437; 568/426; 568/433
[58] Field of Search ................ 568/426, 433, 438, 437

[56] References Cited

U.S. PATENT DOCUMENTS 3,996,290 12/1976 Tavares et al. ..................... 568/433
4,010,207 3/1977 Hall et al. ............................. 568/433

OTHER PUBLICATIONS

Austin, W. B. et al., "Facile Synthesis of Ethynylated Benozic Acid Derivatives and Aromatic Compounds via Ethynyltrimethylsilane," Journal of Organic Chemistry, vol. 46, No. 11 (1981), pp. 2280–2286.

Dawson, D. J. et al., "Cocyclotrimerization of Aryl Acetylenes: Substituent Effects on Reaction Rate," American Chemistry Society Symposium Series:- Polymers for High Technology, vol. 346, ch. 38 (1987), pp. 445–456.

Stephens, R. D. et al., "The Substitution of Aryl Iodides with Cuprous Acetylides, A Synthesis of Tolanes and Heterocyclics," Journal of Organic Chemistry, vol. 28 (Dec. 1963), pp. 3313–3315.

Castro, C. E. et al., "Copper (II) Substitutions, Scope and Mechanism of Cuprous Acetylide Substitutions", Journal of the American Chemical Society, vol. 91 (Nov. 5, 1969), pp. 6464–6470.

Onopchenko, A. et al., "Selective Catalytic Hydrogenation of Aromatic Nitro Groups in the Presence of Acetylenes, Synthesis of (3-Amino-phenyl) acetylene via Hydrogenation of Dimethylcarbinol Substituted (3-Nitrophenyl) acetylene over Heterogeneous Metallic Ruthenium Catalyst," Journal of Organic Chemistry, vol. 44, No. 8 (1979).

Primary Examiner—Werren B. Lone
Attorney, Agent, or Firm—Gary G. Borda; Charles D. Miller

[57] ABSTRACT

A method of producing an ethynyl aromatic aldehyde comprises reacting a protected copper(I) acetylide salt with a halogen substituted aromatic compound to produce a protected ethynyl aromatic aldehyde.

The protected ethynyl aromatic aldehyde may be deprotected to yield an acetylene terminated aromatic aldehyde which is useful for making acetylenic Schiff's base monomers and conductive polymers thereof.

12 Claims, No Drawings

SYNTHETIC METHOD FOR ETHYNYLATION OF AROMATIC COMPOUNDS

BACKGROUND OF THE INVENTION

This invention relates to a method of ethynylation of aromatic rings. More particularly, this invention relates to a method of ethynylating aromatic rings by reacting a protected acetylenic carbinol with a halogen substituted aromatic aldehyde to yield a protected ethynyl aromatic aldehyde, which can be subsequently deprotected to yield an ethynyl aromatic aldehyde.

The synthesis of ethynyl aromatic aldehydes is of importance because these compounds may be used to make Schiff's base resins which polymerize into highly useful materials, e.g., conducting polymers. The current method of ethynylating aromatic compounds is described by Austin et. al., J. Org. Chem. 46, 2280 (1981), who react a starting material, such as 3-bromobenzaldehyde, with a two-fold excess of ethynyltrimethylsilane in the presence of palladium(II) acetate and triphenylphosphine. This step is carried out in deaerated, anhydrous triethylamine at reflux under argon. The 3-[(trimethylsilyl) ethynyl] benzaldehyde thus formed is treated with base in anhydrous methanol to give the corresponding ethynylated benzaldehyde. This method suffers the dual disadvantages of expensive reagents and environmentally damaging waste products. There is currently a great need for a method of ethynylating aromatic compounds using inexpensive reagents and producing limited environmentally harmful waste.

Accordingly, it is an objective of the present invention to provide a method of ethynylating aromatic aldehydes without using expensive reagents or producing unnecessary environmentally damaging waste.

SUMMARY OF THE INVENTION

In seeking to achieve the above-stated objectives, there is provided a method of producing a protected ethynyl aromatic aldehyde by reacting a protected copper (I) acetylide salt of formula I:

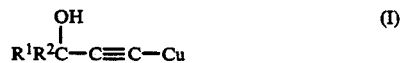

(I)

wherein $R^1$ and $R^2$ are each independently $C_{1-12}$ alkyl or $C_{3-12}$ cycloalkyl, or $R^1$ and $R^2$ together with the carbon to which they are joined form a $C_{3-12}$ cycloalkyl ring; with a halogen-substituted aromatic aldehyde of formula II:

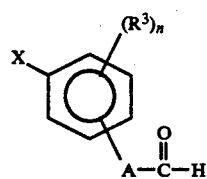

(II)

wherein the A—CHO substituent is ortho, meta, or para to X; X is a halogen; A is a single bond or a group with a continuous pi electron system conjugated to the aldehyde carbonyl; each $R^3$ is any non-interfering ring substituent; and n is 0, 1, 2, 3 or 4; to produce a protected ethynyl aromatic aldehyde of formula III:

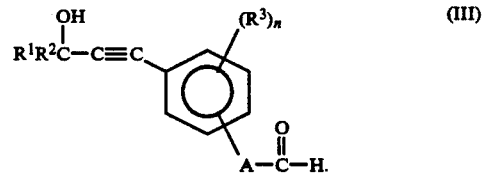

(III)

There is also provided a three step method of ethynylating aromatic aldehydes, which comprises (a) reacting an acetylenic carbinol with a copper (I) halide to form a copper (I) salt of said acetylenic carbinol, (b) reacting the copper (I) salt of the acetylenic carbinol with a halogen substituted aromatic aldehyde to produce a protected ethynyl aromatic aldehyde, and (c) deprotecting the protected ethynyl aromatic aldehyde to produce an ethynyl aromatic aldehyde.

There is further provided a method of producing a protected ethynyl aromatic aldehyde by reacting an acetylenic carbinol with a halogen substituted aromatic aldehyde in the presence of copper (I) ions, palladium chloride, and triphenylphosphine.

DETAILED DESCRIPTION

It has been discovered that halogenated aromatic aldehydes may be ethynylated by their reaction with copper salts of acetylenic carbinols or by their reaction with acetylenic carbinols in the presence of triphenylphosphine, copper (I) ions, and palladium (II) chloride.

The present invention uses acetylenic carbinols in the ethynylation of aromatic rings. By forming an adduct between a carbonyl compound and acetylene, one terminus of the acetylene group is protected during the ring substitution reaction. The choice of carbonyl compound will determine the identity of the acetylenic carbinol used in the reaction. Dawson et. al., ACS Symp. Ser., Vol. 346, 445 (1987), have shown tertiary alcohols to be good leaving groups when used as protecting agents for terminal acetylene intermediates. The preferred embodiment of this invention uses a tertiary acetylenic carbinol, specifically, 1-ethynyl-1-cyclohexanol. Other acetylenic carbinols may also be acceptable if their copper salts are soluble in the reaction solvent, which is typically pyridine.

Suitable ketones for forming tertiary acetylenic carbinols include any ketone with substituents $R^1$ and $R^2$ being any straight or branched $C_{1-12}$ alkyl group or a $C_{3-12}$ cycloalkyl group, preferably a $C_{1-4}$ alkyl group and most preferably methyl or ethyl. Alternatively the ketone can be a $C_{3-12}$ cycloaliphatic ketone preferably cyclopentanone or cyclohexanone. Most preferred ketones are acetone, methyl ethyl ketone (MEK) and cyclohexanone.

$R^3$ is any non-interfering substituent, including, e.g., preferably a $C_{1-12}$ alkyl group, which may be substituted or unsubstituted, a $C_{6-20}$ aryl group, including a fused ring, a $C_{6-20}$-aralkyl or alkaryl group, and the like. $R^3$ is preferably $C_{1-4}$ alkyl, and n is preferably 0 or 1. It will be understood that the benzene ring in Formula II can be replaced by a fused bicyclic or polycyclic ring, although a benzene ring is preferred.

The group A is a single bond or a group containing one or more conjugated double and/or triple bonds that link the aromatic ring with the aldehyde carbonyl. Suitable such pi-electron systems include one or more vinyl or ethynyl groups, another fused or conjugated aromatic ring, preferably homocyclic, or a combination thereof. Preferably, A is a single bond or a fused or conjugated homoaromatic ring.

The present invention's deprotection step regenerates the same ketone used to make the acetylenic carbinol chosen for the protecting group. The isolation of a deprotected product may be facilitated by using an acetylenic carbinol which leads to a ketone easily removed from the typically basic deprotection medium. A volatile ketone, e.g., acetone or MEK, may be removed from the deprotection reaction mixture by evaporation. Additionally, it is preferable to use an acetylenic carbinol which results in a ketone that does not substantially undergo an aldol condensation with the desired product, an ethynylated aromatic aldehyde.

The acetylenic carbinol is reacted with a copper(I) halide salt to form the copper(I) salt of the acetylenic carbinol. In a preferred embodiment of the present invention, cuprous iodide is dissolved in concentrated ammonium hydroxide solution and added dropwise to an ethanol solution of the acetylenic carbinol. Routine skill may be employed to vary the solvents and reaction conditions from the examples described hereafter.

The halogen substituted aromatic aldehyde used as a starting material may be selected depending upon the final product desired. Aromatic aldehydes are the preferred products, but other functional groups are expected to be compatible with the present invention's substitution reaction. The reaction is expected to be enhanced by electron withdrawing groups in the ortho and/or para positions but, by the examples which follow, also is demonstrated to work for an electron withdrawing group in the meta position. The starting material may also contain one or more non-interfering ring substituents. The preferred embodiment of the present invention uses a monocyclic starting material, 3-bromobenzaldehyde; however, the invention is also expected to work for polycyclic aromatic compounds.

The reaction between the copper acetylide salt and the halogen substituted aromatic aldehyde is carried out under an inert atmosphere so as not to promote coupling of the copper acetylide salt. In a preferred embodiment of the present invention bromobenzaldehyde is dissolved in dry pyridine. The copper acetylide salt is added, and the mixture is heated under an argon atmosphere. The resulting precipitate, ethynyl benzaldehyde, is isolated by filtration.

The following examples are intended to illustrate the invention, and do not limit the invention in any way.

EXAMPLE 1

Preparation of Cuprous Acetylide Salt

The copper salt of 1-ethynyl-1-cyclohexanol was prepared as follows. In a 500 ml. erlenmeyer flak equipped with a magnetic stirring bar was placed 14.80 g. (0.077 mole) of cuprous iodide. To this was added 370 ml. of concentrated ammonium hydroxide. The solution was allowed to stir for twenty minutes or until most of the cuprous iodide had dissolved.

In a 1000 ml. erlenmeyer flask equipped with a magnetic stirring bar was placed 10.00 g. (0.080 moles) of 1-ethynyl-1-cyclohexanol in 355 ml. of absolute ethanol. The solution was allowed to stir for half an hour or until the 1-ethynyl-1-cyclohexanol had completely dissolved.

The aqueous ammoniacal solution prepared above was transferred to a separatory funnel and added dropwise to the 1-ethynyl-1-cyclohexanol solution still stirring. The formation of a lightly colored, fluffy precipitate was apparent. After complete addition of the aqueous ammoniacal solution, 1000 ml. of deionized water was added to encourage precipitation. The reaction mixture was allowed to stir for one half hour.

The precipitate was isolated via gravity filtration and washed with two liters deionized water and 500 ml. ether. The ether dissolved the precipitate, and what remained on the filter was a charcoal-gray powder. A 1000 ml. separatory funnel was used to separate the organic layer from the aqueous layer. The aqueous layer was discarded and the organic layer was dried over anhydrous magnesium sulfate. The magnesium sulfate was isolated via gravity filtration and the ethereal solution was placed in a rotary evaporator. A bright canary yellow solid was obtained. The yield was 6.34 g. (53% of theoretical yield), and the solid melted between 100 and 104° C.

EXAMPLE 2

Preparation of Protected Ethynyl Benzaldehyde

The protected ethynyl benzaldehyde was prepared as follows. In a 50 ml. two-necked round bottom flask equipped with a magnetic stirring bar, argon inlet, and a reflux condenser was placed 1.62 g. (0.0087 mol.) of bromobenzaldehyde and 28.3 ml. dry pyridine. The pyridine had been dried over sodium hydroxide pellets and distilled. The flask was purged with argon while stirring and 1.58 g. (0.0084 mol.) of the copper acetylide salt was added during the argon flush. Upon addition of the copper acetylide salt, the reaction mixture became reddish amber in color. The contents were heated in a wax bath at 127.8° C. for eighteen hours. Caution was taken to prevent particles from burning on the sides of the flask by keeping the wax bath below the reaction mixture's volume line. As the reaction progressed, the color of solution turned from a reddish to brownish amber and a darkly colored precipitate had formed. Upon completion of the reaction the solution was cooled and quenched with 85 ml. of deionized water. The precipitate was isolated by suction filtration and washed with approximately 70 ml. of deionized water. Immediately after the wash solution hit the floor of the receiving flask, a tan in color precipitate came out of solution. Upon further addition of wash solution, the precipitate became lighter in color and brown oil droplets lined the bottom of the erlenmeyer flask. What remained on the filter paper was a brownish black precipitate which was subsequently washed with 120 ml. of ether. The ethereal wash solution became tan in color. The combined ethereal and aqueous wash solutions were transferred to a 1000 ml. separatory funnel for separation. After mixing of the ethereal layer and the aqueous layer, the ether layer became darker in color while the aqueous layer took on a light yellowish green color. Two additional extractions with ether, 40 ml. each, were done on the aqueous layer. The combined ether extracts were washed successively with 50 ml. each of 0.1 N. hydrochloric acid, 5% sodium bicarbonate, and deionized water, and dried over magnesium sulfate. The dried ethereal solution was placed in a rotary evaporate at 30° C.; however, not all the solvent evaporated. What remained in the round bottom flask was a brownish amber liquid with an odor characteristic of pyridine. This was put under vacuum (3 mm.) at 75° C. Only a few milliliters of solvent were pulled over; the product remained in solution.

EXAMPLE 3

Deprotection

3-Ethynylbenzaldehyde was prepared from the protected product of Example 2 as follows. Into a 50 ml. two-necked round bottomed flask with an argon inlet was placed a magnetic stirring bar, 21 ml. of methanol, and 0.1 g. of anhydrous potassium carbonate. The coupled product described above was added to the contents of the round bottomed flask for hydrolysis. This remained stirring under argon for several days. After the second full day, a bright yellow precipitate was present. The color of the solution was light amber-yellow. The precipitate (0.1 g) was isolated via suction filtration and washed with methanol. It was then sealed in a vial and placed in the refrigerator for future analysis. The filtrate was transferred to a 100 ml. round bottomed flask and placed in a rotary evaporator at 50° C. Caution was taken to not increase the temperature above 50° C. for fear of possible degradation. However no solvent evaporated. Thus a vacuum of 3 mm. had to be pulled with the reaction mixture at a temperature of 40° C. What was obtained was a wet, dark yellow solid substance. The residue was then mixed with 10 ml. of a near saturated aqueous solution of sodium bicarbonate and extracted with dichloromethane three times, 5 ml. each time. The combined organic fractions were dried over magnesium sulfate. Gravity filtration was used to filter off the magnesium sulfate. The filtrate was transferred to a 100 ml. round bottomed flask and placed in a rotary evaporator at 35° to 45° C. A white thin disk began to form as solvent was evaporating. Thus dry ice and high vacuum (3 mm.) were used to obtain evaporation at lower temperatures. This yielded a very wet, dark yellow solid. Some solvent still remained with a weak scent of pyridine. It was dark yellowish amber in color. Crude yield 1.09 g.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A method of producing an ethynyl aromatic aldehyde, comprising the step of reacting a protected copper (I) acetylide salt of formula I:

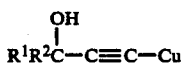
(I)

wherein $R^1$ and $R^2$ are each independently $C_{1-12}$ alkyl or $C_{3-12}$ cycloalkyl, or $R^1$ and $R^2$ together with the carbon to which they are joined form a $C_{3-12}$ cycloalkyl ring; with a halogen-substituted aromatic aldehyde of formula II:

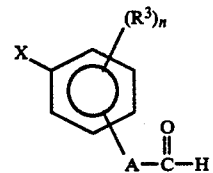
(II)

wherein the A—CHO substituent is ortho, meta, or para to X; X is either bromine or iodine; A is a single bond or a group with a continuous pi electron system conjugated to the aldehyde carbonyl; $R^3$ is any non-interfering ring substituent; and n is 0, 1, 2, 3 or 4; to produce a protected ethynyl aromatic aldehyde of formula III:

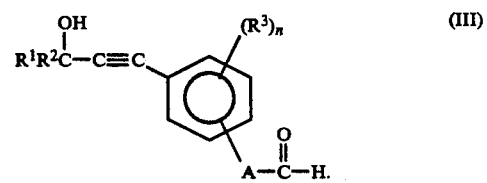
(III)

2. A method according to claim 1, wherein said copper (I) acetylide salt is formed by reacting an acetylenic carbinol with cuprous iodide or bromide.

3. A method according to claim 1, wherein $R^1$ and $R^2$ are each $CH_3$.

4. A method according to claim 1, wherein $R^1$ and $R^2$ together with the carbon to which they are joined form a cyclohexane ring.

5. A method according to claim 1, wherein n equals zero.

6. A method according to claim 1, wherein A is a single bond.

7. A method according to claim 6, wherein the CHO group is meta to X.

8. A method according to claim 1, wherein said protected ethynyl aromatic aldehyde is subsequently deprotected to produce an ethynyl aromatic aldehyde of formula IV:

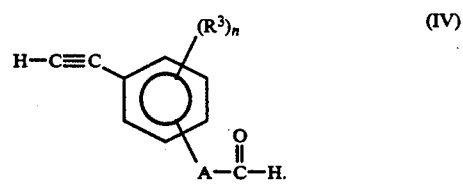
(IV)

9. A method according to claim 8, wherein said protected ethynyl aromatic aldehyde is deprotected in a basic medium.

10. A method of producing an ethynyl aromatic aldehyde, comprising the steps of:
   (a) reacting an acetylenic carbinol with cuprous iodide to form a copper (I) salt of formula I:

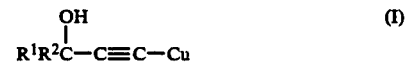
(I)

wherein $R^1$ and $R^2$ are each independently $C_{1-12}$ alkyl or $C_{3-12}$ cycloalkyl, or $R^1$ and $R^2$ together with the carbon to which they are joined form a $C_{3-12}$ cycloalkyl ring;

(b) reacting said copper (I) salt of said acetylenic carbinol with a halogen substituted aromatic aldehyde of formula II:

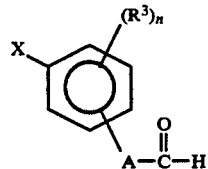

wherein the A—CHO substituent is ortho, meta, or para to X; X is either bromine or iodine; A is a single bond or a group with a continuous pi electron system conjugated to the aldehyde carbonyl; $R^3$ is any non-interfering ring substituent; and n is 0, 1, 2, 3 or 4; to produce a protected ethynyl aromatic aldehyde of formula III:

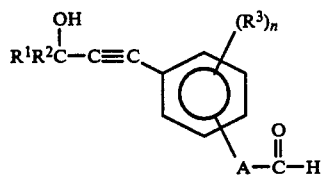

and (c) deprotecting said protected ethynyl aromatic aldehyde in a basic medium to produce an ethynyl aromatic aldehyde of formula IV:

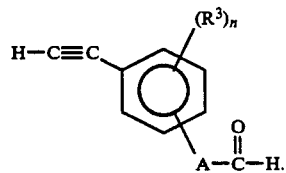

11. A method of producing an ethynyl aromatic aldehyde comprising reacting an acetylenic carbinol of formula V:

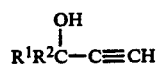

wherein $R^1$ and $R^2$ are each independently $C_{1-12}$ alkyl or $C_{3-12}$ cycloalkyl, or $R^1$ and $R^2$ together with the carbon to which they are joined form a $C_{3-12}$ cycloalkyl ring; with a halogen-substituted aromatic aldehyde of formula II:

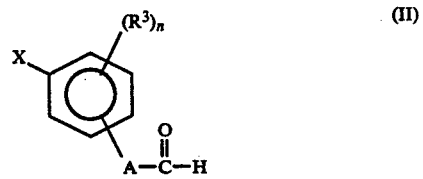

wherein the A—CHO substituent is ortho, meta, or para to X; X is either bromine or iodine; A is a single bond or a group with a continuous pi electron system conjugated to the aldehyde carbonyl; $R^3$ is any non-interfering ring substituent; and n is 0, 1, 2, 3 or 4; in the presence of copper (I) ion, triphenylphosphine, and palladium chloride to produce a protected ethynyl aromatic aldehyde of formula III:

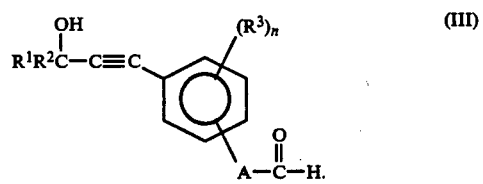

12. A method according to claim 11, wherein said protected ethynyl aromatic aldehyde is subsequently deprotected to produce an ethynyl aromatic aldehyde of formula IV:

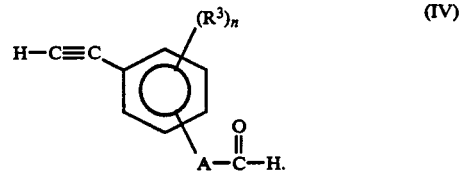

* * * * *